(12) United States Patent
Stromberg et al.

(10) Patent No.: US 9,422,518 B2
(45) Date of Patent: *Aug. 23, 2016

(54) HIGH SOLIDS ENZYME REACTOR OR MIXER AND METHOD

(75) Inventors: Bertil Stromberg, Diamond Point, NY (US); John F. Bolles, Queensbury, NY (US); Thomas Pschorn, Sherbrooke, CA (US); Peter Mraz, Klosterneuburg (AT)

(73) Assignee: Andritz Inc., Glens Falls, NY (US)

( * ) Notice: Subject to any disclaimer, the term of this patent is extended or adjusted under 35 U.S.C. 154(b) by 2 days.

This patent is subject to a terminal disclaimer.

(21) Appl. No.: 13/879,330

(22) PCT Filed: Oct. 14, 2011

(86) PCT No.: PCT/US2011/056342
§ 371 (c)(1),
(2), (4) Date: May 7, 2013

(87) PCT Pub. No.: WO2012/051523
PCT Pub. Date: Apr. 19, 2012

(65) Prior Publication Data
US 2013/0224852 A1    Aug. 29, 2013

Related U.S. Application Data

(60) Provisional application No. 61/393,740, filed on Oct. 15, 2010.

(51) Int. Cl.
*C12M 1/02*    (2006.01)
*C12M 1/10*    (2006.01)
(Continued)

(52) U.S. Cl.
CPC .............. *C12M 27/02* (2013.01); *C12M 23/02* (2013.01)

(58) Field of Classification Search
CPC .... C12M 27/02; C12M 35/04; C12M 23/14; C12M 29/10; C12M 21/04; C12M 27/20; C05F 17/0235; C05F 17/0258; C05F 17/0205; C05F 17/02; B01F 7/1635; B01F 7/1645; B01F 7/1675; B01F 13/0827; B01F 7/00175; B01F 7/1695; B01F 7/00208; B01F 2215/0032; B01F 13/002; B01F 2003/125; B01F 13/0035; B01F 9/06; B01F 2215/005; A61K 9/1694
USPC .......... 435/290.1–290.4, 292.1; 366/278, 348
See application file for complete search history.

(56) References Cited

U.S. PATENT DOCUMENTS 4,806,477 A * 2/1989 Rothert et al. ................. 435/177
5,837,506 A   11/1998 Lynd et al.
(Continued)

FOREIGN PATENT DOCUMENTS

| EP | 0 573 892 A1 | 12/1993 |
| JP | 2006-055761 | 3/2006 |
| WO | 98/30710 A1 | 7/1998 |

OTHER PUBLICATIONS

International Search Report cited in PCT/US2011/056342 mailed Feb. 28, 2012.
(Continued)

*Primary Examiner* — Michael Hobbs
(74) *Attorney, Agent, or Firm* — Nixon & Vanderhye P.C.

(57) ABSTRACT

A reactor apparatus including: an internal mixing chamber including a first chamber section having a cross-sectional area expanding from a biomass inlet to the internal mixing chamber to the a second chamber section; the second chamber section having a substantially uniform internal cross-sectional area from the opposite end of the first chamber section to a discharge end of the mixing chamber; the biomass inlet is coupled to a source of pre-treated biomass external to the reactor vessel, and a rotating mixing device in the internal mixing chamber and coaxial with an axis of the first chamber section.

21 Claims, 3 Drawing Sheets

(51) Int. Cl.
*C12M 1/06* (2006.01)
*C12M 1/00* (2006.01)

(56) References Cited

U.S. PATENT DOCUMENTS 6,296,384 B1* 10/2001 Yatomi et al. ............... 366/147
6,346,412 B1* 2/2002 Stormo ......................... 435/262
8,617,355 B2* 12/2013 Romero ................. C12M 21/18
    127/37
2005/0019913 A1* 1/2005 Condon et al. ............... 435/373
2007/0029252 A1 2/2007 Dunson et al.

OTHER PUBLICATIONS

Korean Patent Office, Grounds for Rejection (with translation), 17 pages, Nov. 27, 2014.

* cited by examiner

HIGH SOLIDS ENZYME REACTOR OR MIXER AND METHOD

RELATED APPLICATION

This application is a U.S. national phase application of PCT/US2011/056342 filed 14 Oct. 2011 and claims priority to U.S. Provisional Utility Application 61/393,740 filed on Oct. 15, 2010, the entirety of which are incorporated by reference.

BACKGROUND OF THE INVENTION

This invention relates generally to the field of enzymatic conversion of biomass to monomeric sugars and particularly to mixing the biomass with enzymes to promote hydrolysis.

Biomass feedstock may be solely lignocellulosic material or a mixture of lignocellulosic and other materials. Polysaccharide biomass is typically a mixture of starch and lignocellulosic materials. The starch may be contained in grains or a refined starch added as feedstock to form the biomass. The biomass feedstock may also include polymers and other materials.

Enzymes, such as cellulose, are mixed with the biomass to promote hydrolysis. Mixing ensures that the enzymes continually and repeatedly move into contact with chemical reaction sites in the biomass. In addition or in place of enzymes other cellulose degrading organisms and biocatalysts, such as thermophilic bacterium or yeast, may be added to the biomass to promote hydrolysis or other degradation of the biomass.

The different feedstock materials and enzymes (or other degrading materials) are mixed together to form the biomass mixture. The biomass mixture may have characteristics similar to a high matter content powder. Liquid may also be added to the biomass mixture to form a high liquid slurry. Liquid is added to liquefy biomass solids and generate a uniform biomass emulsion formed of feedstock and liquids which have significant differences in their characteristics.

Mixers, constant stir reactors and other such mixing or agitation devices may be used to mix and liquefy the feedstock and enzymes to form the biomass mixture. These devices conventionally are cylindrical vessels arranged vertically and having mechanical mixing devices, such as stirrers having radial arms and blades. These mixing devices generally rotate about a vertical shaft and move through the biomass. The period of mixing needed for the biomass mixture depends on the feedstocks used to form the biomass.

Enzymatic liquefaction of lignocellulosic biomass may require several hours of mixing. This mixing process reduces the viscosity of the biomass as the biomass converts from a generally solids composition to a liquefied slurry. Biomass pretreated for enzymatic conversion to monomeric sugars typically starts the mixing process having a fibrous or mud-like consistency. The enzymes added to the biomass typically have a relatively low concentration with respect to the biomass. The biomass and enzyme mixture tends to be highly viscous as it enters a mixing and pretreatment reactor system, which include one or more hydrolysis reactor vessels.

Due to the high viscosity of the biomass entering the hydrolysis reactor vessel, a large force (torque) is needed to turn the mixing devices and properly mix the enzymes with the biomass. The mixing speed of the mixing arms and other mixer components in the mixing chamber is typically below 300 revolutions per minute (rpm). The required mixing force traditionally limits the size of the mixing vessels. The conventional mixing devices tend to be small diameter vessels because the torque needed to rotate the mixing arms increases exponentially with the radial length of the arms. Due to the high viscosity of the biomass, the radial length of the arms is traditionally been short so that the can be moved arms through the biomass. Similarly, the motors that turn the mixing arms have maximum power limitations that constrain the maximum length of the mixing arms. Due to the constraints of the motor and the mechanical strength of the mixing components, the vessels for mixing the highly viscous pre-treated biomass have conventionally been small and narrow.

Further, the mixing vessels for enzymatic liquefaction of lignocellulosic biomass have traditionally been operated in a batch mode rather than a continuous mode. Batch mode is often better suited to situations were several smaller mixing vessels feed a larger downstream vessel, such as a digester or other reactor vessel.

Recirculation of liquefied material to dilute the incoming pretreated biomass has been proposed to decrease the viscosity, and improve the mixing. Recirculation has a disadvantage in that additional mixing volume is required to achieve the desired retention time in the vessel. Batch processing adds volume to the system, as time has to be provided to fill and empty the vessel.

There is a need for large mixing vessels capable of mixing highly viscous biomass with enzymes. These vessels would preferably be continuous flow vessels in which biomass flows continuously in, through and out of the vessel. A large vessel would provide efficient, high flow capacity for mixing biomass and enzymes.

BRIEF DESCRIPTION OF THE INVENTION

A novel apparatus and method is disclosed herein for mixing, e.g., liquefaction, of biomass. The apparatus and method may be used for the liquefaction and saccharification of polysaccharide containing biomasses, which may have a dryer matter content of above 10% w/w (weight/weight). The apparatus and method combines enzymatic hydrolysis with a mixing process that relies on physical forces, such as gravity and centrifugal force, to ensure that the biomasses are subjected to mechanical forces, such as shear and tear forces.

The apparatus and method disclosed herein may be applied in processes of biomasses, such as for fermentation of biomass to bio-alcohols such as ethanol or butanol, forming bio-gas, forming specialty carbohydrates for food and feed, forming carbo-hydrate feedstock and for processing biomass into plastics and chemicals.

A mixing and reactor vessel is disclosed herein comprising: an internal mixing chamber including a first chamber section having a cross-sectional area expanding from a biomass inlet to the internal mixing chamber to the a second chamber section, the second chamber section having a substantially uniform internal cross-sectional area from the opposite end of the first chamber section to a discharge end of the mixing chamber; the biomass inlet is coupled to a source of pre-treated biomass external to the reactor vessel, and a rotating mixing device in the internal mixing chamber and coaxial with an axis of the reactor vessel.

A method is disclosed herein to mix biomass and an enzyme in a reactor and mixing vessel comprising the steps of: feeding the biomass and enzyme to an to the vessel, wherein the inlet is aligned with a narrow end of a first internal mixing chamber of the vessel; moving and mixing the biomass and enzyme as they flow from the narrow end to a wide end of the first internal mixing chamber section wherein the first internal mixing chamber expands in cross-section along a movement direction of the biomass and enzyme through the chamber; moving and further mixing the mixture of biomass and enzyme from the first internal mixing chamber to a second internal mixing chamber having a substantially uniform cross-sectional area in the movement direction; discharging from the vessel the biomass and enzyme mixture from a discharge outlet of the second internal mixing section. This mixture of biomass and enzyme may be an enzyme such as cellulose, a thermophilic bacterium or other cellulose degrading organism or biocatalyst.

The first internal mixing chamber may have multiple zones at different elevations in the vessel. These zones may be separated via optional and possibly adjustable bottoms, e.g., baffles or trays, in the vessel to optimize a step-wise transformation of the biomass solids to a slurry. These intermediate bottoms are preferably horizontal and extend substantially the entire cross-section of the vessel at the elevation where the platform is positioned. The bottoms may also be slightly inclined with respect to horizontal. Adjustable openings in the intermediate bottoms may be provided to vary the flow through the bottoms and from one zone to the next one. Depending on the dry matter feedstock and mixing slurry in question (which could be an enzyme mixture), that may be no intermediate bottoms in the vessel such that the downward movement of the biomass mixture is dependent solely on gravity and plugflow downflow of the induced matter through the reactor vessel.

The already conditioned (liquefied) slurry flows from lower zones (or the bottom) of the mixing vessel. A portion of the slurry flow may be pumped or circulated to upper zones in the vessel to adjust the slowly changing viscosity of the biomass feedstock at the upper elevations of the vessel.

The conical top may provide approximately constant torque as the material flows through the mixer. The angle of the cone could change as the diameter increases, as the viscosity decrease is fast in the beginning and then slows down. The vessel top may also consist of several stacked concentric cylinders with increasing diameters from top to bottom.

DETAILED DESCRIPTION OF THE INVENTION

Figure 1:
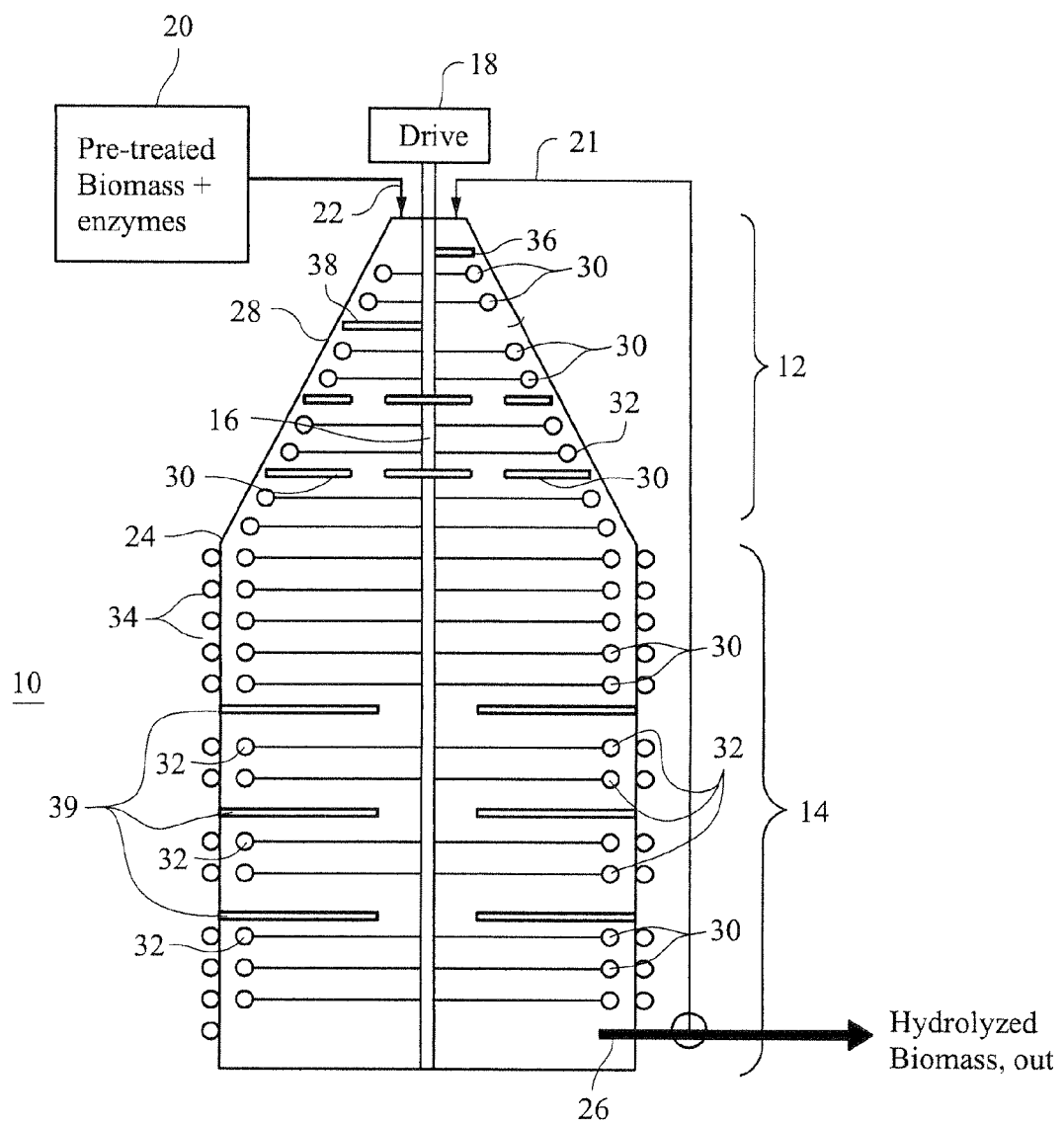
FIG. 1 is a schematic diagram showing in cross-section a vertically aligned mixing and hydrolysis reaction vessel for biomass.

FIG. 1 shows schematically a reactor and mixing vessel 10 having a conical upper section 12 and a cylindrical lower section 14. These sections 12, 14 define an internal reaction chamber in which the biomass is mixed with the enzyme(s) and is hydrolyzed. The internal reaction chamber may have a volume in a range of 50 cubic meters to 2,500 cubic meters. Narrower ranges of 200 cubic meters to 1,200 cubic meters or 400 cubic meters to 800 cubic meters will also be suitable depending on the specific application of the reaction and mixing process. The reaction chamber may be substantially larger in volume than batch mixing/reactor vessels conventionally used to mix highly viscous biomass.

The vessel includes a rotatable shaft 16 extending along the vertical axis of the vessel. The shaft is driven (rotated) by a motor and gear box drive assembly 18, which may be mount to the top or bottom of the vessel. The shaft 16 may be to a vertical axis of the vessel and extend the height of the vessel. The shaft turns a mixing device 28, e.g., mixing arms and paddles, that moves through and churn the biomass in the vessel.

A source 20 of biomass and enzymes may be continuously fed to an upper inlet 22 of the vessel 10. The biomass and enzymes may be fed as a mixture to the vessel or fed separately to the vessel. The source 20 may include a short retention time horizontal mixer, in which the biomass and enzymes are brought into initial contact with each other. If desired, recycled low viscosity hydrolyzed material 21 is introduced into the source 20 or the upper inlet 22 of the vessel.

The inlet 22 feeds the biomass to a narrow region of the conical upper section 12. The cross-sectional area of the upper section 12 expands from the upper narrow region to the transition 24 between the upper section 12 and the lower section 14. The cross-section area of the lower section 14 may be uniform along its entire height. The bottom of the lower section is adjacent a discharge outlet 26 for the hydrolyzed biomass continuously flowing out of the vessel 10 to other process units, such as a digester, fermenter or continuing enzymatic hydrolysis vessels. The bottom of the lower section may be sloped to provide a uniform discharge from the entire cross-sectional area of the bottom of the lower section.

A mixing device 28 (shown schematically by a tree of rotating arms 30 in FIG. 1) is mounted to the shaft 16 and rotates through the biomass and enzymes moving downward through the upper and lower sections 12, 14 of the vessel. The mixing device 28 may include radially extending arms or spokes 30 at various elevations in the vessel. The arms may extend horizontally or may be oblique with respect to horizontal. The arms 30 may be arranged as spokes extending from the shaft. The arms may have mixing paddles, blades or fingers 32 arranged at the radial end of the arms and optionally at various positions along the radial length of each of the arms.

The arms 30 may be adjusted to be positioned at various elevations and positions in the vessel. Similarly, the paddles, blades or fingers 32 may be adjustably mounted on each of the arms. The adjustment may change, for example, the angle at which the paddles, blades or fingers are oriented with respect to the direction of rotation of the arms. The orientation of the paddles, blades or fingers may be set to provide a slight radially outward flow to the biomass to distribute the biomass evenly through the cross-sectional area of the vessel. The rotation of arms with the paddles, blades or fingers at one or more elevations or radii may be provide may also apply a slight uplift of the biomass to prevent short-circuiting of the biomass flowing down from above through the vessel.

The arms turn in a circular rotational pattern through the biomass in the vessel. The arms are turned by the rotating shaft 16. The movement of the arms and mixing paddles, blades or fingers mix the enzyme into the biomass and thereby cause the enzyme to come into contact with reaction sites in the biomass. The reactions between the enzyme and the biomass promotes hydrolysis of the biomass in the vessel.

Mixing baffles 32 may be installed on the inside vessel wall of the lower section 14 and optionally the upper section 12. The biomass flowing through the lower section will have a relatively low viscosity, as compared to the viscosity at the vessel inlet. Mixing baffles are most suitable for low viscosity flows through a mixing vessel. Trays or baffles could also be installed between the mixing arms to aid in distribution of the biomass material.

The shaft and mixing arms may provide indirect cooling or heating to the biomass, such as by cooling or heating passages in the arms. Similarly, the interior walls of the vessel may be jacketed or provided with cooling or heating coils 34.

As an example, to hydrolyze 1200 tons of biomass per day, where the biomass has a 25% solids loading, the reactor vessel should be sized to process about 5000 cubic meters of biomass during a twenty-four (24) hour retention period in the vessel. The vessel should be larger if the biomass retention period is longer, such as 72 to 120 hours. A vessel having an internal chamber volume of 15,000 cubic meters to 25,000 cubic meters may be needed to provide long retention periods of a continuous flow of a large amount of biomass, e.g., 1200 tons/day, being hydrolyzed.

The diameter, height and other dimensions of the vessel depend on the flow of biomass and retention period of the biomass in the vessel. By way of example, a reactor vessel 10 may need an effective internal volume of about 1200 cubic meters to handle 1200 tons of biomass per day at a 25 percent solids loading and a six hour retention period. Assuming that the aspect ratio (diameter to height) of the vessel is six, the diameter of the vessel would be about 5.4 meter and its height would be greater than 33 meters.

The conical upper section 12 is narrowest at the upper inlet that receives the highly viscous biomass entering the vessel. The viscosity of the biomass is greatest at the top inlet to the vessel. While the high viscosity increases the starting torque needed to turn the mixing device, the torque is lessened because of the short mixing arms at the narrow top. The biomass becomes less viscous as it mixes it the enzyme and moves down through the vessel. The lessening viscosity allows for the mixing arms to be longer without increasing the torque needed to turn shaft. The arms in the lower portions of the upper conical section are longer than most or all the upper arms 30. Longer arms require more torque to be turned through the biomass, assuming the viscosity of the biomass remains constant. The combined effects of the reduction in viscosity of the biomass and the longer arms results in acceptable torque requirements for the mixing device in the upper conical section.

The conical geometry of the upper section reduces the starting torque requirement. Less power is required for mixing, the biomass can be more thoroughly mixed, and the biomass is less susceptible to channeling down through the vessel. The conical shape also results relatively frequent and robust mixing near the inlet of the vessel, where mixing may be most beneficial to promote hydrolysis.

Torque increases with the diameter squared. The torque required to move (mix) a fluid in a circle is a function of the force required to move the fluid times the radius of that force from the center of rotation. The force required to move the fluid is a function of the viscosity of the fluid, the velocity of the motion and the distance that the fluid has to move.

Assuming a constant fluid viscosity and constant rotation of the mixing device, the torque required to turn the mixing device depends on the square of the radius of the vessel. Due to the squared relationship between torque and vessel diameter, reducing the vessel diameter dramatically reduces the amount of torque or allows the same amount of torque to mixing a highly viscous biomass flow.

The conical upper section 12 is suited for short mixing arms in the upper region of the vessel where viscosity is high. The shortest mixing arms are at the top of the vessel where the biomass viscosity is greatest and the resistance of the biomass to mechanical mixing is high. As the biomass moves down through the upper section, the viscosity of the biomass lessens, the resistance to mixing decreases and longer mixing arms may be used in view of the increasing diameter of the conical portion of the vessel.

By knowing the viscosity of the biomass at various elevations in the upper section 12, the angle of the cone of the upper section may be selected such that the radius of the mixing arms increases at a rate that results in uniform torque on the arms at each elevation. Thus, each mixer arm may require the same torque to mix the material, even through the diameter of the conical section is increasing in a downward direction.

Intermediate bottoms, trays or baffles 38 may be installed and adjusted to separate the upper section 12 into multiple zones to optimize a step-wise transformation of the biomass mixture to a slurry with a higher liquid content than the original biomass. The zones may be generally vertically aligned in the vessel. These intermediate and adjustable bottoms may be horizontal in the vessel and may also be slightly inclined with respect to horizontal. Further, adjustable openings in the intermediate bottoms may be used to vary the flow between the zones defined by the bottoms. Similarly, intermediate bottoms, trays and baffles 39 may be arranged in the lower section 14 into multiple zones.

Figure 2:
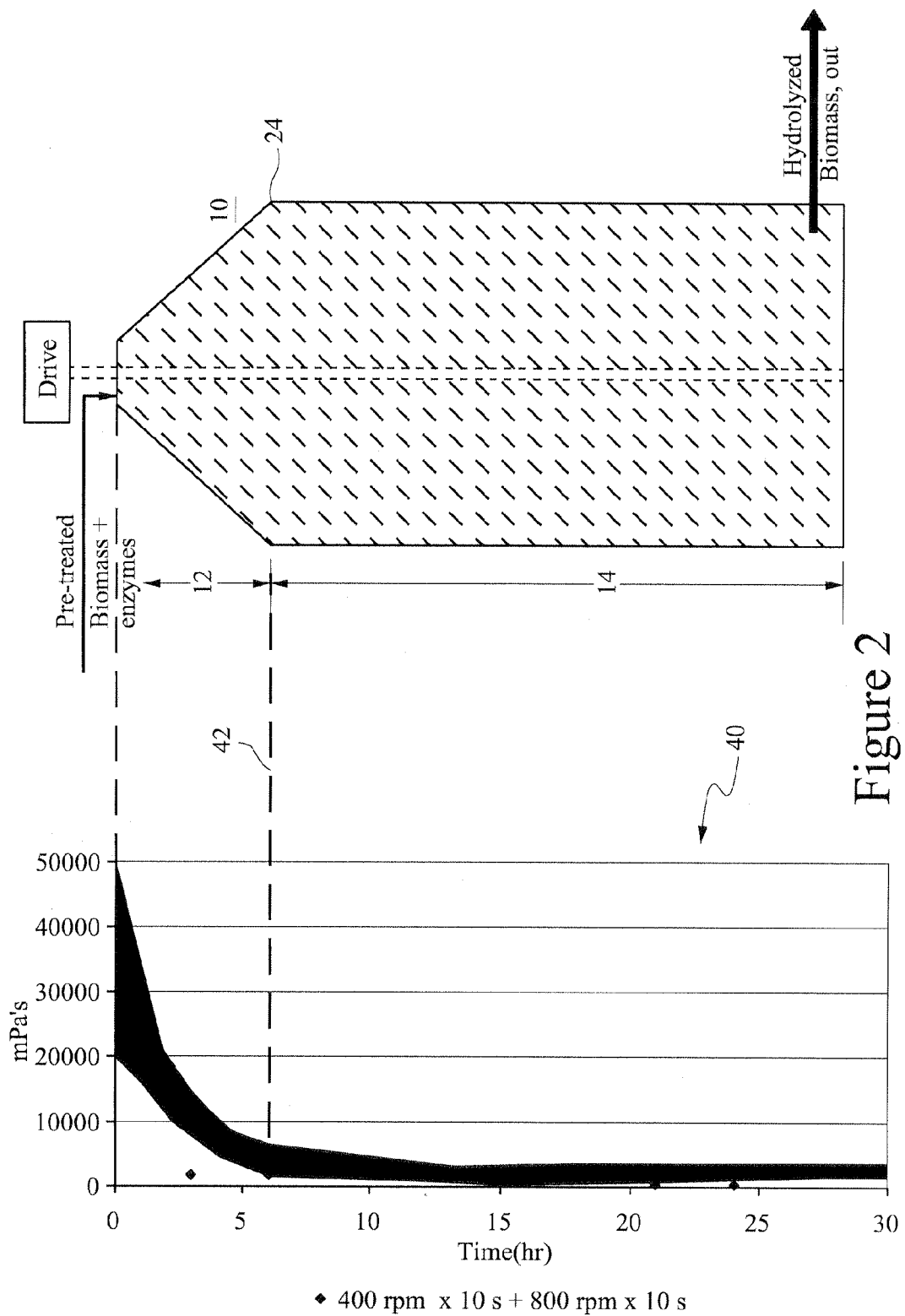
FIG. 2 is a chart showing an expected viscosity of the biomass in the reaction vessel shown in FIG. 1 as a function of retention time of the biomass in the vessel.

FIG. 2 includes a chart 40 of viscosity of the biomass in the vessel 10 as a function of time. The chart is for illustrative purposes. The chart shows the viscosity of a biomass which is steam exploded corn stover mixed at a temperature of 50 degrees Celsius and in a vessel having mixing devices rotating at 20 rpm. The chart shows a range of viscosity values in milliPascal-second (mPas) for the biomass undergoing saccharification. The range results from two different starting mixing patterns used for the biomass.

As shown in the chart 40, the viscosity of the biomass may reduce quickly such that the viscosity has been reduced by one-half or more after six hours of reaction time in the vessel. It is known that only about six (6) hours of reaction time (or somewhat more reaction time) is needed in the vessel to convert the viscous biomass flow to a flowing, syrupy consistency. During this initial reaction period (e.g., 15 minutes to 8 hours, preferably 1 hour to 6 hours, most preferably 2 hours to 4 hours), the apparent viscosity of the biomass decreases quickly as enzymes break down the polymeric sugars of the biomass to smaller molecule chains.

The downward flow rate of the biomass through the vessel can be calculated or estimated by conventional means. As illustrated in FIG. 2, the reaction time of biomass in a continuous flow vessel 10 correlates with the movement of the biomass down through the vessel. The vessel may have the mixing device, heating coils and intermediate bottoms as shown in FIG. 1. The continuous biomass flow through the vessel is represented by diagonal dashes shown in the illustration of the vessel.

Using the rate of flow through the vessel and the reaction time to reduce the biomass viscosity to a certain level, such as a 50% or less viscosity reduction, the vertical distance down through the vessel can be calculated to determine at which elevation/reaction time 42 the biomass will have a viscosity of one-half the viscosity of the biomass entering the vessel. The conical upper section 12 may be designed such that the transition 24 to the lower cylindrical section 14 occurs at the same elevation where the viscosity of the biomass is reduced by half.

Figure 3:
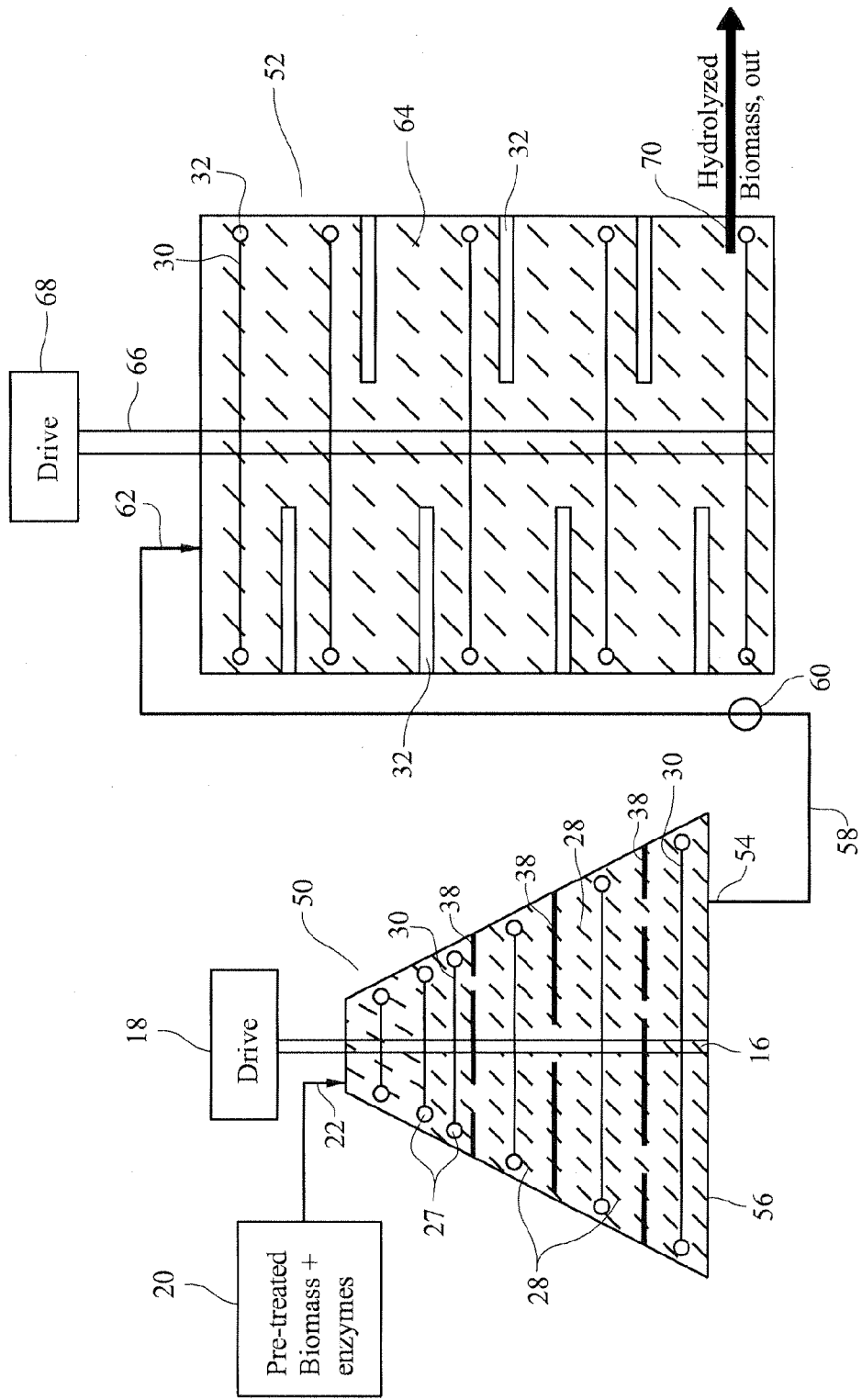
FIG. 3 is a schematic diagram showing in cross-section a conical mixing and hydrolysis vessel connected to a cylindrical mixing and hydrolysis reaction vessel.

FIG. 3 is a schematic diagram showing in cross-section a conical mixing and hydrolysis vessel 50 connected to a cylindrical mixing and hydrolysis reaction vessel 52. The biomass flowing through these vessels is indicated by diagonal dashes. The conical mixing and hydrolysis vessel 50 is similar in many respects to the conical portion of the vessel 10 shown in FIG. 1, as is indicated by the common reference numerals in FIGS. 1 and 3.

Biomass and enzymes are fed from a source 20 to the upper inlet 22 of the narrow end of the conical mixer and reaction chamber 50. A mixing device 28 has arms 36 that increase in length as the conical mixer increases in diameter. Intermediate bottoms, e.g., baffles, trays or other plates 38, may be arranged in the conical vessel to regulate the downward flow of biomass through the vessel. The viscosity of the biomass falls as the biomass is mixed and reacts in the vessel 50. The viscosity may be reduced by half as the biomass is discharged from the vessel at port 54, as compared to the viscosity of the biomass 20 entering the vessel. A tapered or sloped bottom 56 may direct the biomass into the port 54.

A transport conduit, e.g., pipe, 58 and a pump 60 may be used to transport the liquefied biomass to an upper inlet port 62 of the cylindrical vessel 52. The cylindrical vessel includes a mixing device 64 and optionally baffles 32. The mixing device is connected to a shaft 66 driven by a drive and gear assembly 68. The hydrolyzed biomass is discharged at port 70 from the cylindrical vessel.

The invention has now been described in detail for purposes of clarity and understanding. However, it will be appreciated that certain changes and modifications to the disclosed embodiment of the invention may be practiced within the scope of the appended claims.

What is claimed is:

1. A reactor apparatus comprising:
an internal mixing chamber including a first chamber section having a cross-sectional area expanding from a biomass inlet for the internal mixing chamber to a second chamber section including a biomass outlet;
wherein the first chamber section is conical and the cross-sectional area of the first chamber increases continuously along a height of the first chamber section;
wherein the second chamber section has a substantially uniform internal cross-sectional area from an opposite end of the first chamber section to a discharge end of the mixing chamber;
wherein the biomass inlet is configured to be coupled to a source of pre-treated biomass external to the reactor vessel;
a rotating mixing device is the internal mixing chamber coaxial with an axis of the first chamber section and extending through the first chamber section and the second chamber section, wherein the rotating mixing device has multiple arms at successive positions along the axis of the first chamber and the second chamber, wherein the arms at each of the successive positions along the axis of the first chamber section are separate from the arms at the other successive positions along the axis and the length of the arms at one successive position is greater than the arms at another one of the successive positions such that the lengths of the arms in the first chamber section successively increase as the cross-sectional area of the first chamber section increases, and
wherein the reactor apparatus includes an enzyme inlet coupled to a source of an enzyme.

2. The reactor apparatus as in claim 1 wherein the second chamber section is cylindrical.

3. The reactor apparatus as in claim 1 wherein the first chamber and the second chamber are within a single reaction vessel, and the first chamber is above the second chamber.

4. The reactor apparatus as in claim 1 wherein the mixing device includes arms extending radially from a rotating shaft coaxial with the axis.

5. The reactor apparatus as in claim 1 wherein the internal mixing chamber has a volume of at least 50 cubic meters.

6. The reactor apparatus as in claim 1 wherein the internal mixing chamber has a retention time of 15 minutes to 8 hours.

7. The reactor apparatus as in claim 1 wherein the inlet coupled to the source of an enzyme is the biomass inlet which receives the biomass and the enzyme as a mixture.

8. The reactor apparatus as in claim 1 wherein the axis of the apparatus is vertical and the biomass inlet is at an upper elevation of the apparatus and the discharge end is at a lower elevation of the apparatus.

9. The reactor apparatus of claim 1 wherein the axis is vertical and the biomass inlet is at a lower elevation of the apparatus and the discharge end is at an upper elevation of the apparatus.

10. The reactor apparatus as in claim 1 wherein the source of an enzyme is a source of thermophilic bacterium.

11. The reactor apparatus as in claim 1 wherein the reactor apparatus includes an inlet coupled to a source of a cellulose-degrading organism.

12. The reactor apparatus of claim 1 wherein the reactor apparatus includes an inlet coupled to a source of a biocatalyst.

13. An enzymatic reactor vessel assembly comprising:
a first conical mixing chamber having a cross-sectional area expanding from a biomass inlet to the assembly to an outlet of the first conical mixing chamber;
a second reactor chamber receiving biomass from the biomass outlet of the first conical mixing chamber, the second reactor chamber section having a substantially uniform internal cross-sectional area from the outlet of the first conical mixing chamber to a discharge end of the second reactor chamber, wherein the discharge includes a biomass outlet of the assembly;
the biomass inlet being coupled to a source of pre-treated biomass external to the reactor vessel; and
a rotating mixing device in the reactor vessel assembly, coaxial with an axis of the first conical mixing chamber and extending through the first conical mixing chamber and second reactor chamber, wherein the rotating mixing device has multiple arms and the arms are a successive positions along the axis of the first conical mixing chamber and the second reactor chamber, wherein the arms at each of the successive positions in the first conical mixing chamber have a length greater or less than a length of the arms at another one of the successive positions in the first conical mixing chamber such that the lengths of the arms in the first conical mixing chamber successively increase as the cross-sectional area of the first conical mixing chamber increases; and
wherein the first mixing chamber includes an enzyme inlet coupled to a source of an enzyme.

14. The enzymatic reactor vessel as in claim 13 wherein the first conical mixing chamber is in a first apparatus and the second reactor chamber is in second chamber and is in fluid communication with the first conical mixing chamber apparatus.

15. The enzymatic reactor vessel assembly as in claim 13 wherein the first conical mixing chamber has a cross-sectional area which increases linearly.

16. The enzymatic reactor vessel assembly as in claim 13 wherein the second reactor chamber is cylindrical.

17. The enzymatic reactor vessel assembly as in claim 13 wherein the first mixing chamber and the second chamber are within a single reaction vessel, and the first conical mixing chamber is above the second reactor chamber.

18. The enzymatic reactor vessel assembly as in claim 13 wherein the mixing device includes arms extending radially out from a rotating shaft.

19. The enzymatic reactor vessel assembly as in claim 13 wherein the first conical mixing chamber and second reactor chamber have a combined volume of at least 50 cubic meters.

20. The enzymatic reactor vessel assembly as in claim 13 wherein the first conical mixing chamber and second reactor chamber are continuous flow chambers having a combined retention time of 15 minutes to 8 hours.

21. The enzymatic reactor vessel assembly as in claim 13 wherein the source of an enzyme consists of a source of at least one of an enzyme, thermophilic bacterium, cellulose degrading organism, and a biocatalyst.

\* \* \* \* \*